(12) United States Patent
Wu et al.

(10) Patent No.: US 11,573,223 B2
(45) Date of Patent: Feb. 7, 2023

(54) EXTRACTION REAGENT OF IMMUNOSUPPRESSANT DRUG FOR IMMUNOASSAYS

(71) Applicant: SHANGHAI INZEX BIOTECHNOLOGY CO., LTD., Shanghai (CN)

(72) Inventors: Fengbo Wu, Shanghai (CN); Yongyan Nie, Shanghai (CN); Xiaojuan Shi, Shanghai (CN)

(73) Assignee: Shanghai Inzex Biotechnology Co., Ltd., Shanghai (CN)

( * ) Notice: Subject to any disclaimer, the term of this patent is extended or adjusted under 35 U.S.C. 154(b) by 350 days.

(21) Appl. No.: 16/838,889

(22) Filed: Apr. 2, 2020

(65) Prior Publication Data

US 2020/0232975 A1     Jul. 23, 2020

Related U.S. Application Data

(62) Division of application No. 15/549,952, filed as application No. PCT/CN2015/080330 on May 29, 2015, now abandoned.

(30) Foreign Application Priority Data

Mar. 30, 2015 (CN) .......................... 201510145431.1

(51) Int. Cl.
| | | |
|---|---|---|
| *G01N 33/53* | (2006.01) | |
| *G01N 33/94* | (2006.01) | |
| *G01N 33/50* | (2006.01) | |
| *G01N 33/543* | (2006.01) | |
| *G01N 33/487* | (2006.01) | |
| *G01N 33/577* | (2006.01) | |
| *G01N 1/44* | (2006.01) | |
| *G01N 1/40* | (2006.01) | |
| *G01N 1/28* | (2006.01) | |
| *G01N 33/533* | (2006.01) | |
| *G01N 33/537* | (2006.01) | |
| *G01N 1/38* | (2006.01) | |

(52) U.S. Cl.
CPC ....... *G01N 33/5306* (2013.01); *G01N 1/4022* (2013.01); *G01N 1/4044* (2013.01); *G01N 1/44* (2013.01); *G01N 33/487* (2013.01); *G01N 33/50* (2013.01); *G01N 33/577* (2013.01); *G01N 33/9493* (2013.01); *G01N 33/533* (2013.01); *G01N 33/5375* (2013.01); *G01N 2001/388* (2013.01)

(58) Field of Classification Search
CPC ...... G01N 1/4022; G01N 1/4044; G01N 1/44; G01N 1/28; G01N 2001/388; G01N 33/487; G01N 33/49; G01N 33/50; G01N 33/54; G01N 33/5406; G01N 33/533; G01N 33/5375; G01N 33/54333; G01N 33/577; G01N 33/9493; G01N 33/543; Y10T 436/10; Y10T 436/107497; Y10T 436/108331; Y10T 436/171538; Y10T 436/25; Y10T 436/255
USPC ..... 435/7.1, 12, 23; 436/518, 531, 536, 538, 436/540, 9, 17, 18, 63, 86, 108, 174, 178
See application file for complete search history.

(56) References Cited

U.S. PATENT DOCUMENTS

| | | | |
|---|---|---|---|
| 4,895,799 A | 1/1990 | Kruse-mueller et al. | |
| 5,089,390 A | 2/1992 | Davalian et al. | |
| 7,575,875 B2* | 8/2009 | Konrath | G01N 33/9446 422/417 |
| 7,883,855 B2* | 2/2011 | Grenier | G01N 33/9493 435/7.1 |
| 7,914,999 B2* | 3/2011 | Grenier | G01N 33/5306 435/7.1 |
| 8,221,986 B2* | 7/2012 | Grenier | G01N 33/9493 435/7.1 |
| 8,465,966 B2 | 6/2013 | Ewert | |
| 2003/0152524 A1 | 8/2003 | Eshita | |
| 2004/0209353 A1 | 10/2004 | Chien et al. | |
| 2006/0177855 A1 | 8/2006 | Utermohlen et al. | |

(Continued)

FOREIGN PATENT DOCUMENTS

| | | |
|---|---|---|
| CN | 1147853 A | 4/1997 |
| CN | 1260173 A | 7/2000 |

(Continued)

OTHER PUBLICATIONS

Wu et al. Analytical Biochemisry, vol. 576, pp. 13-19, Apr. 10, 2019.*

(Continued)

*Primary Examiner* — Maureen Wallenhorst
(74) *Attorney, Agent, or Firm* — Dorsey & Whitney LLP

(57) ABSTRACT

A reagent for extracting immunosuppressant drugs from a whole blood sample for immunoassay includes protein denaturant, proteolytic enzyme, surfactant and pH buffer. A method and an immunoassay kit for detection of the immunosuppressant concentration in a whole blood sample uses the extraction reagent. The extraction reagent doesn't need the use of organic solvent as that in the traditional extraction methods, therefore the adverse effects of the organic solvent on the antibody activity in a detection system and the other relative defects associated to its use are obviated. The drug extraction process doesn't need centrifugation, as the processed sample can be directly applied for immunoassay. The operation for drug extraction is simple, and the detection result based on this extraction method is accurate.

14 Claims, 9 Drawing Sheets

(56) References Cited

U.S. PATENT DOCUMENTS

| | | | |
|---|---|---|---|
| 2006/0216762 A1* | 9/2006 | Belenky | G01N 33/9493 435/7.21 |
| 2007/0026435 A1 | 2/2007 | Templer | |
| 2008/0020401 A1* | 1/2008 | Grenier | G01N 33/9493 435/7.1 |
| 2009/0182120 A1 | 7/2009 | Utermohlen et al. | |
| 2011/0136136 A1* | 6/2011 | Wei | G01N 33/9493 435/7.1 |
| 2014/0087366 A1 | 3/2014 | Srinivasan et al. | |
| 2016/0008809 A1 | 1/2016 | Li et al. | |

FOREIGN PATENT DOCUMENTS

| | | |
|---|---|---|
| CN | 1369266 A | 9/2002 |
| CN | 101664394 A | 3/2010 |
| CN | 101946179 A | 1/2011 |
| CN | 102939524 A | 2/2013 |
| CN | 104160273 A | 11/2014 |
| EP | 753744 * | 1/1997 |
| EP | 0717850 | 5/1997 |
| JP | H06289016 A | 10/1994 |
| JP | 2003235587 A | 8/2003 |
| JP | 2010515063 A | 5/2010 |
| JP | 2010515065 A | 5/2010 |
| JP | 2012002593 A | 1/2012 |
| WO | 93/25533 * | 12/1993 |
| WO | 2008/082979 * | 7/2008 |
| WO | 2008/082984 * | 7/2008 |
| WO | 2016155111 A1 | 10/2016 |

OTHER PUBLICATIONS

International Search Report for International Patent Application No. PCT/CN2015/080330, dated Jan. 6, 2016 (4 pages).

Li, et al., "Denaturation Study of Bovine Serum Albumin Induced by the Guanidine Chloride or Urea by Microcalorimetry," Acta Chimica Sinica, Mar. 14, 2008, p. 516, vol. 66, No. 5.

* cited by examiner

EXTRACTION REAGENT OF IMMUNOSUPPRESSANT DRUG FOR IMMUNOASSAYS

CROSS REFERENCE TO RELATED APPLICATIONS

This application is a divisional of U.S. patent application Ser. No. 15/549,952 filed 9 Aug. 2017, now abandoned, entitled "An extraction reagent of immunosuppressant drug for immunoassays," which is a national phase filing of Patent Cooperation Treaty application no. PCT/CN2015/080330 filed 29 May 2015 entitled "Immunosuppressant drug extract reagent for immunoassay," which claims priority to Chinese patent application no. 201510145431.1 filed 30 Mar. 2015 entitled "Immunosuppressant drug extract reagent for immunoassay," which are each hereby incorporated herein by reference in their entirety.

TECHNICAL FIELD

The present disclosure relates to the field of in vitro diagnostic reagents, in particular to an improved extraction reagent of immunosuppressant drug, and an extraction method and immunoassay kit using the extraction reagent, which can be used for determining the concentration of an immunosuppressant in whole blood sample of a patient.

BACKGROUND

Immunosuppressant is a class of chemical or biological substances used to alleviate tissue damage by inhibiting the cellular and humoral immune responses, and has been widely used for anti-rejection after organ transplantation and for treatment of autoimmune diseases, such as rheumatoid arthritis, lupus erythematosus, ankylosing spondylitis and autoimmune hemolytic anemia, etc.

Five types of immunosuppressants are mainly used presently: microbial metabolic products, glucocorticoids, antimetabolites, antilymphocyte antibodies and alkylating agents, of which microbial metabolic products such as Tacrolimus (FK506), Cyclosporin A (CsA) and Rapamycin (Rapa) etc. are most widely used because of their potent effect on inhibiting the activation and proliferation of T lymphocytes, mainly by suppressing the activity of calcineurin in cytoplasm and blocking the transcriptions of a series of cytokines such as IL2, etc.

For medication of transplantation patients, insufficient dose of immunosuppressant may give rise to immunologic rejection, while overmedication with immunosuppressant may be toxic for organs such as the liver and kidney, and causes a series of adverse clinical events including infections and tumors. Therefore, reasonable medication of the transplantation recipients requires accurate monitoring of the blood level of these drugs. As commonly used immunosuppressants, tacrolimus, sirolimus and Cyclosporin-A exist mainly in red blood cells bound by proteins despite of the difference in their molecule structure. In order to accurately measure the blood concentration of these drugs, they must be liberated from the binding proteins, and this is the common requirement for the monitoring of blood immunosuppressant drugs.

Current methods for the quantification of blood immunosuppressant mainly include ligand-receptor binding assay, high-performance liquid chromatography-tandem mass spectrometry (HPLC-MS/MS), microparticle enzyme immunoassay (MEIA), chemiluminescent microparticle immunoassay (CMIA) and enzyme-linked immunosorbent assay (ELISA), etc. Among these, ligand-receptor binding assay is used mainly for pharmaceutical research. HPLC-MS/MS is accurate and sensitive, but is mainly used as a reference method because of its inconvenience in operation, long detection time and high cost. MEIA and CMIA are the routine clinic choice for immunosuppressant measurement due to their accurate test results and high degree of automation. However, above methods require the use of organic solvent such as methanol, acetonitrile and diethyl ether, etc. as the extraction reagent to dissolve cells and extract drugs. This not only brings inconvenience for the performing the analysis, but also impair the sensitivity and accuracy of the immunoassay by inhibiting the immunoreaction between the antibodies and drugs, impairing the affinity of antibodies and causing fluctuation of drug concentration via volatilization of the organic solvent in the extraction reagent.

In order to alleviate the adverse effect of the organic solvent on the anti-FK506 antibody binding to FK506, Robert W. Siegel et al. (Clinical Chemistry, 2008, 54: 6, 1008-1017; U.S. Pat. No. 8,022,188 B2) modified the complementary determining region of the antibody by gene mutagenesis, and based on this, improved the detection sensitivity. However, this method requires complicated manipulations including DNA extraction, amplification, sequencing, mutagenesis, cloning and screening etc., so it is not easy to be realized in most laboratories. In order to depress the fluctuation of drug concentration caused by the volatilization of the organic solvent, Frank C. Grenier et al. used low volatile reagent such as DMSO to formulate the drug extraction reagent (US 2008/0020401 A1), but DMSO used in the method also inhibits the binding of antibodies to the drugs obviously. Moreover, just like the above-mentioned organic solvent based extraction reagents, it contains high concentration of divalent metal ions (10 mM-100 mM) to lyse cell, and this can cause additional errors when the concentration of divalent metal ions is inconsistent in different test caused by different amount of the anticoagulation EDTA in each samples.

Moreover, the samples processed by above organic solvent based extraction reagents are nonhomogeneous with precipitated proteins in it, and so need to be centrifuged to remove the precipitate; this step makes the extraction tedious and prolongs the detection time.

In order to avoid the adverse effects of the organic solvent on immunoassay, François Legay et al. proposed a method for FK506 detection with RAPA to displace FK506 from its binding-proteins (U.S. Pat. No. 6,187,547 B1). As FK506 and RAPA in blood share the same binding proteins (mainly the FK-binding protein) with only a small part of the drugs bound by serum albumin and lipoprotein, and both FK506 and RAPA can penetrate cell membranes rapidly due to their high hydrophobicity, the bound FK506 in blood can be effectively replaced by high concentration of RAPA, this makes it unnecessary to lyse cell and denature protein for FK506 release. In this method, RAPA in the reaction mixture does not disturb the FK506 detection because of the high specificity of anti-FK506 monoclonal antibody used. By omitting the extraction steps, the FK506 immunoassay was simple and rapid, and can get accurate measurement for most samples without interference components in it. However, this methods will give wrong results for measuring samples with interference factors in it, especially when patients are remedied with drugs of antibody type.

Therefore, a drug extraction method without the need to use the organic solvent is in urgent need for rapid, simple and accurate detection of the immunosuppressant drugs.

Currently, such an extraction reagent and extraction method which have above-mentioned characteristics has not been reported at home and abroad.

SUMMARY

In order to obviate the above-mentioned adverse effects of the organic solvent-based extraction reagent on immunoassays, the present disclosure provides a new extraction reagent and a method of using it for in immunoassay of immunosuppressant drugs in blood sample. The extraction reagent consists of protein denaturant, proteolytic enzyme, surfactant and pH buffer. The drug extraction comprises steps of mixing the sample with extraction reagent at a suitable proportion and incubating the mixture to release the intracellular drugs under the action of protein denaturant and protease. The extraction reagent of the present disclosure can effectively lyse blood cells and release the intracellular drugs without the use of organic solvent. Compared with the existing extraction reagent, the present method can avoid the fluctuation of the drug concentration caused by volatilization of the organic solvent, and alleviate the inhibition of the antibody binding to drug by the organic matrix. Moreover, the whole blood samples can be turned into entirely homogeneous solution after being processed with the extraction reagent of the present disclosure and applied to immunoassay directly without centrifugation; this simplifies the sample processing procedure and shortens the detection time.

Therefore, the first purpose of the present disclosure is to provide an extraction reagent for extracting immunosuppressant from a blood sample.

The second purpose of the present disclosure is to provide a method for measurement of the immunosuppressant concentration in a blood sample.

The third purpose of the present disclosure is to provide a kit for measuring the concentration of immunosuppressant in blood sample.

In order to achieve the above-mentioned purposes, the present disclosure provides technical solutions as follows:

According to the first aspect of the present disclosure, an extraction reagent for extracting an immunosuppressant from a blood sample comprises protein denaturant, proteolytic enzyme, surfactant and pH buffer.

According to the present disclosure, the protein denaturant is selected from urea, guanidine hydrochloride or other non-organic solvent based denaturants.

According to a preferred embodiment, the protein denaturant is urea.

According to the present disclosure, the concentration of the urea in the extraction reagent is 4 mol/L to 12 mol/L, preferably, 6 mol/L to 8 mol/L. The molar concentration of the guanidine hydrochloride in the extraction reagent is 1 mol/L to 8 mol/L, preferably, 2 mol/L to 6 mol/L.

According to the present disclosure, the proteolytic enzyme is selected from subtilisin (from *Bacillus subtilis*), protease K and dispase, etc., or a mixture thereof; preferably, the proteolytic enzyme is subtilisin.

According to the present disclosure, the amount of the subtilisin in the extraction reagent is 1 U/ml to 20 U/ml, preferably, 2.5 U/ml to 10 U/ml.

According to the present disclosure, the surfactant is selected from one or more of TWEEN®-20 (polysorbate-20), saponin and TRITON® X-100 (polyethylene glycol octyl phenyl ether); preferably, it is TWEEN®-20 (polysorbate-20).

According to the present disclosure, the volume ratio of TWEEN®-20 (polysorbate-20) in the extraction reagent is 0.005%-1% (v/v), preferably, 0.02%-0.1% (v/v).

According to the present disclosure, the pH of the buffer is in the range of 6.5 to 8.5, preferably, 7.0-8.0.

According to the second aspect of the present disclosure, a method for measuring the concentration of immunosuppressant in blood sample, comprises steps of incubating the blood sample with the extraction reagent under a heating condition to dissolve blood cells and release drug via the synergistic effect of the protein denaturant, proteolytic enzyme and surfactant, and then converting the blood sample into a homogeneous solution which can be directly used in immunoassay without centrifugation and finally obtain accurate measurement of the target drug.

According to the present disclosure, the immunosuppressant comprises tacrolimus, sirolimus, everolimus, zotarolimus, cyclosporin A or other structural analogues.

According to the present disclosure, the blood sample is from an organ transplantation patient or other patients taking immunosuppressants.

According to the present disclosure, when mixing the extraction reagent with the blood sample, the volume ratio of the blood sample to the extraction reagent is 1/1 to 1/10, preferably 1/2 to 1/5.

According to the present disclosure, blood sample is processed under heating condition, the heating temperature is 50° C.-90° C.; preferably it is 60° C.-80° C.

According to the present disclosure, the time of heating for the blood sample processing is 5 min to 50 min, preferably 10 min to 30 min.

According to the present disclosure, the effect of the extraction reagent and method is to dissolve cells, release the drug and convert the blood sample to a homogeneous solution.

According to the present disclosure, the immunoassay is a competitive inhibition method based on the mode: the immunosuppressant in the sample competitively bind to a limited amount of anti-immunosuppressant antibody with a fixed amount of immunosuppressant.

According to the present disclosure, the immunoassay is a solid phase immunoassay, the typical embodiment of which is: immobilizing an immunoreagent on the surface of a solid phase container, after the competitive immunoreaction, separating the free detection reagent from the bound one to realize the concentration measurement of the analyte.

According to the present disclosure, the solid phase container refers to a microwell, test tube or a container of other forms.

According to the present disclosure, the immunoassay comprises following steps:

1) Blood sample processing. Mixing the sample with the extraction reagent, heating the mixture and then recovering it to room temperature.

2) Immunoreaction. Adding the processed sample, anti-immunosuppressant antibody and a fixed amount of the immunosuppressant in a container; or alternatively, adding the processed sample, a fixed amount of a labelled immunosuppressant and anti-immunosuppressant antibody in a container. The immunosuppressant released from the sample competitively bind to the anti-immunosuppressant antibody with the fixed amount of the immunosuppressant, and the immune complexes are captured by the solid phase reagent.

3) Separation. Separating the free detection reagent from the bound detection reagent by washing.

4) Detection. Measuring the signals generated from the tracer substances contained in the immune complexes captured by the solid phase reagent, calculating the concentration of the immunosuppressant according to the calibration curve obtained by plotting the signal intensity versus immunosuppressant concentration.

The blood sample refers to anticoagulant whole blood sample, including whole blood sample anticoagulated by EDTA-K (Na), sodium citrate (potassium) and heparin; preferably, it is whole blood anticoagulated by EDTA-K (Na).

According to the third aspect of the present disclosure, a kit for quantification of immunosuppressant in blood sample comprises: a) anti-immunosuppressant antibody, b) the extraction reagent, c) immunosuppressant, d) calibrators, and e) buffer solution. Wherein, the antibody or immunosuppressant is labelled by a tracer and used as a detection reagent.

According to a preferred embodiment of the present disclosure, the anti-immunosuppressant antibody refers to an antibody which can specifically bind to an immunosuppressant drug, and it can be a polyclonal or monoclonal antibody; preferably, it is a monoclonal antibody.

According to the present disclosure, the extraction reagent consists of a protein denaturant, proteolytic enzyme, surfactant and pH buffer.

According to the present disclosure, the detection reagent refers to an antibody, antigen or immunosuppressant hapten which has been labelled by a tracer substance.

According to the present disclosure, the tracer substance refers to a substance which can trigger a detectable signal, including but not confined to an enzyme, chemiluminescent substance, radioactive substance, fluorescent substance, rare earth ion (such as $Eu^{3+}$, $Sm^{3+}$, $Tb^{3+}$, $Dy^{3+}$) and chelate ligands thereof, it can also be indirect small molecular tracer such as biotin and digoxin, etc.

According to the present disclosure, the buffer solution consists of pH buffer solution, protein, surfactant and other reagent for reducing interference, it is used for diluting the immunoassay reagent, reducing the background signal and relieving the interference by heterophilic antibody etc.

According to the present disclosure, the calibrator refers to a solution or freeze dried product containing a known concentration of the immunosuppressant, it is used for establishing a calibration curve. In order to reduce the matrix effect, the present disclosure uses human whole blood as the matrix to formulate the calibrator.

Beneficial Effects

The extraction reagent of the present disclosure keeps the following advantages of the traditional organic solvent-based extraction reagents:

It can dissolve cells and release the drug rapidly and effectively.

It can inactivate interfering substances derived from the samples such as heterophilic antibody and rheumatoid factor, etc.

At the same time, the extraction reagent of the present disclosure has following advantages which don't exist in traditional organic solvent-based extraction reagents:

1) It doesn't contain volatile organic solvent, so the possibility of fluctuation of the drug concentration caused by solvent volatilization is omitted.

2) It doesn't contain an organic solvent, so the inhibition of the immunoreaction between the antibody and drug by the organic solvent is avoided, and the sample extraction and the sample processing after the experiment are more simple.

3) It doesn't contain any divalent metal ions, so the concentration variation of the divalent metal ions and its effect on drug extraction, caused by the different amount of anticoagulant in individual samples, is avoided.

4) The blood samples processed by the extraction reagent of present disclosure is an entirely homogeneous solution and can be directly applied to immunoassay without centrifugation. This simplifies the operation and shortens the detection time of the assay.

5) A more reliable measurement result can be obtained.

6) Based on above characteristic, the detection using the present extraction reagent is more convenient to be applied to automatic equipment, and makes it easier to develop the fully automatic detection equipment.

The effectiveness of the present extraction reagent originates from its effectiveness for dissolving cells, denaturing proteins and releasing drug. Therefore, the present disclosure can be used not only for extracting immunosuppressant from human blood sample, but also can be used for extraction of other drugs or non-drug substances from human blood and blood samples of various animals.

DETAILED DESCRIPTION OF THE EMBODIMENTS

Figure 1:
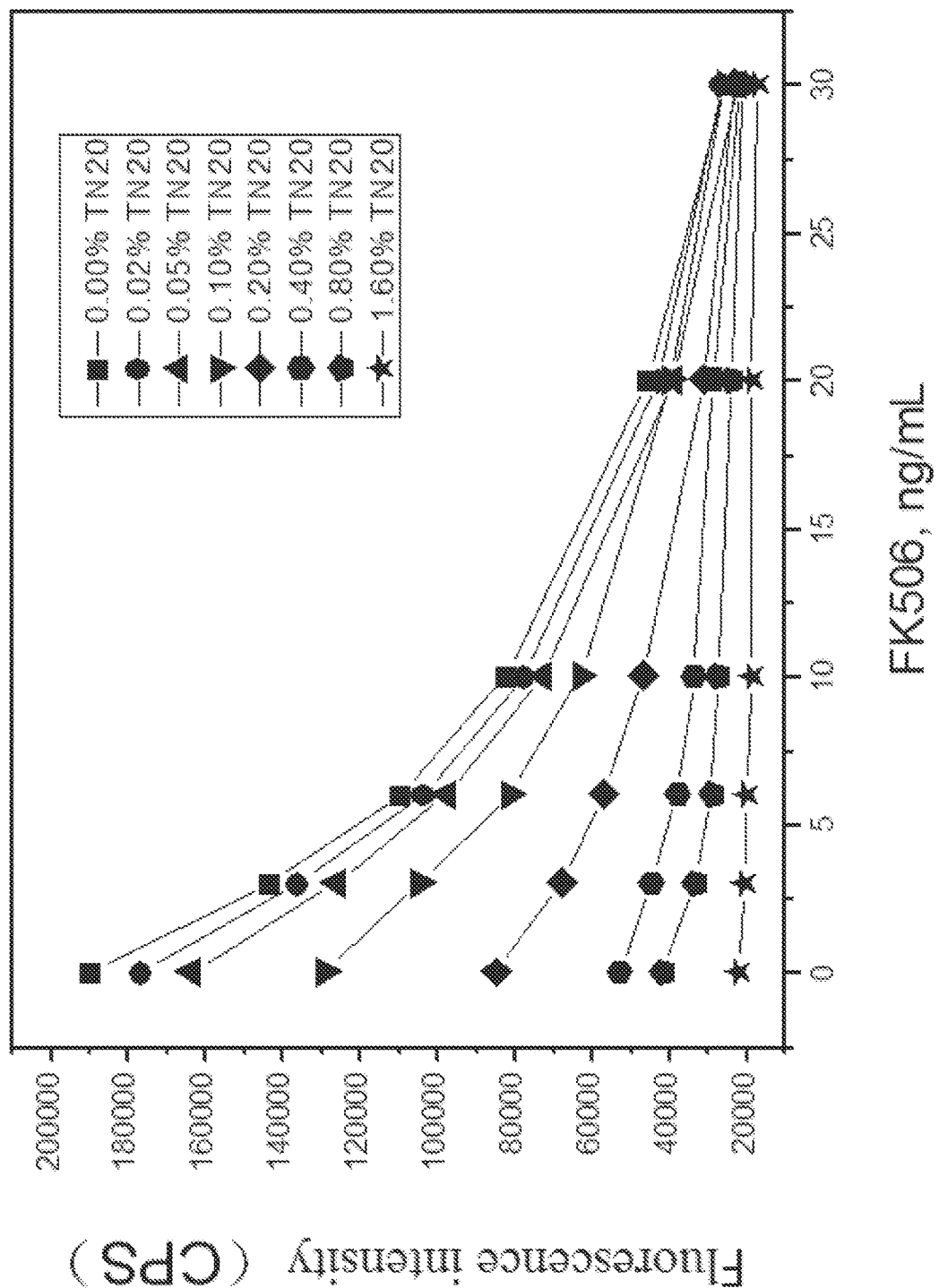
FIG. 1 shows the effect of TWEEN®-20 (polysorbate-20) at different concentrations in the extraction reagent on the FK506 extraction.

Unless otherwise stated, the claims and description use the definitions according to the following explanations.

I. Immunosuppressant

The immunosuppressant refers to a class of drugs that suppress the strength of the body's immune system by inhibiting the proliferation of immune cells and the related functions; preferably, the immunosuppressant of the present disclosure refers to tacrolimus (FK506), sirolimus (Rapa), everolimus, zotarolimus or cyclosporin A.

II. Extraction Reagent

The extraction reagent of the present disclosure is a mixture of protein denaturant, proteolytic enzyme, surfactant and pH buffer, which can rapidly dissolve cells and release the protein-bound immunosuppressant by the synergistic effect of the protein denaturant, the proteolytic enzyme and the surfactant.

III. Immunosuppressant Extraction

The immunosuppressant extraction of the present disclosure refers to a process of releasing the immunosuppressant from its binding protein of the sample and converting it into a detectable ingredient.

Mixing a blood sample with the extraction reagent at an appropriate proportion; preferably, 10 μl-50 μl of blood sample is mixed with 50 μl-200 μl of extraction reagent; more preferably, 25 μl of blood sample is mixed with 170 μl of extraction reagent. After been mixed by vortexing, the mixture was heated and incubated for a period of time. The incubation temperature and time is selected to make sure that under this condition immunosuppressant drugs can be efficiently released, and in the meanwhile the enzyme can be effectively inactivated at the end of the extraction process. Generally, the incubation temperature is 50° C.-90° C., and the incubation time is 5 min-50 min; preferably, it is 10 min-30 min at 60° C.-80° C. After incubation, the mixture of blood sample and extraction reagent becomes a homogeneous solution and can be applied for immunoassay directly.

IV. Immunoassay

Immunoassay refers to an analytical method for detection of substances based on the specific interaction between antibody and antigen (or hapten). The immunoassay of present disclosure is used for quantitative measurement of immunosuppressant. The immunoassay kit of present disclosure is mainly composed of extraction reagent, antibody, a fixed amount of analyte or its analog for competitive binding to the antibody with the analyte in the sample, assay buffer and calibrator. Different immunoassay modes can be applied with either of antibody and analyte labelled as the detection reagent.

The effectiveness of the extraction reagent of the present disclosure originates from its high potency for dissolving cells, denaturing protein and releasing drugs, therefore, the present disclosure can not only be applied for extracting immunosuppressant from human blood sample, but also can be used for extracting other drugs or non-drug substances which are present in a binding state in blood samples of human being or other various kinds of animals; preferably, the sample of the present disclosure is anticoagulant whole blood sample of patients taking immunosuppressant.

The immunoassay kit also comprises an instruction for describing how to use the kit. The instruction can be can be fixed to the outer packaging of the kit or stored in the kit in the form of a separate sheet. The instruction can be a printed or handwritten material, or any medium which can store the instruction and transmit the information to an end user, comprising but not limited to electronic storage media, such as optical or magnetic disks.

Urea is a commonly used protein denaturant and used as the main component of the extraction reagent of the present disclosure. When urea is used at a high concentration, it can form double hydrogen bond with the carbonyl oxygen atoms of two adjacent peptide bond on a protein backbone, destructing the secondary and tertiary structures of the protein, making the peptide chain of protein fully stretched and so losing its original physical/chemical and biological properties. However, when urea is at a low concentration, its action on denaturing protein is significantly decreased. Based on the property, 6 mol/L-10 mol/L of urea can be used to dissolve cells, denature proteins and release the immunosuppressant. And in the meanwhile, the adverse effect of urea on the binding activity of antibody in the immunoreaction solution is significantly lowered when the small amount of the sample processed by the extraction reagent is added in a container and diluted to 1/10-1/5 of its initial concentration by buffer.

Subtilisin is another key component of the extraction reagent of the present disclosure. Subtilisin expresses its maximum of proteolytic activity at 60° C.-80° C., but this activity lasts only short period of time due to the its deactivation at the same temperature (Niu Shuyi and Han Baoqin, Purification and enzymatic properties of subtilisin from *Bacillus subtilis*, Biotech world, 2014, 3: 11-12). Accordingly, the enzyme can function well at 60° C.-80° C. to promote cell lysis and protein denaturation, and in the meanwhile most of the enzyme activity is inactivated after the incubation. The residual activity of the enzyme in the extracted sample is further decreased when it is recovered to room temperature (Niu Shuyi and Han Baoqin, Purification and enzymatic properties of subtilisin from *Bacillus subtilis*, Biotech world, 2014, 3: 11-12) and diluted by the buffer after the extraction. Above three factors further decreased the effect of the residual enzyme activity on the binding activity of the antibody.

Surfactant is another main component of the extraction reagent of the present disclosure, the main function of it is to promote cell lysis in cooperation with urea and the protease and to make the blood become a homogeneous solution. Strong surfactants such as SDS is effective for cell lysis but exert severe adverse effect on antibody activity. Nonionic surfactants, e.g., TWEEN®-20 (polysorbate-20), show good synergetic action for cell lysis and solubilisation, and also contribute to lower the background signal of the immunoassay.

The present disclosure is illustrated in further detail with following specific embodiments. It should be understood that the following embodiments are used only to illustrate the disclosure without limiting the scope of the disclosure.

In the following embodiments, unless noted otherwise, all blood samples need to be processed with the extraction reagent of the present disclosure before the immunoassay is performed for measurement.

In the following embodiments, unless noted otherwise, the related % is a mass/volume ratio (w/v).

Embodiment 1. FK506-TRFIA (Time Resolved Fluorescence Immunoassay)

The FK506-TRFIA in the embodiment is a competitive immunoassay with a second antibody coated on solid phase. In the immunoassay, a processed calibrator/sample, anti-FK506 monoclonal antibody and biotin labelled FK506 were added to microwells coated with goat anti-mouse antibody, wherein the biotin labelled FK506 and the FK506 in the calibrator or sample competitively bind to the limited amount of anti-FK506 monoclonal antibody. The immune complexes formed are captured to the microwell-surface by the immobilized goat anti-mouse second antibody. The unbound biotin labelled FK506 was removed by washing, and then the europium ion ($Eu^{3+}$) labelled streptavidin (SA-$Eu^{3+}$) was added to bind to biotin in the immune complexes on the microwell surface. The unbound SA-$Eu^{3+}$ was washed away, $Eu^{3+}$ in the immune complexes was measured using a dissociation-enhancement solution which dissociates the Eu$^{3+}$ from the microwell surface to form a stable fluorescent complex. The FK506 concentration was determined via a calibration curve established by plotting the fluorescence intensity versus FK506 concentration of the calibrators.

The basic formula of the present extraction reagent is 50 mM Tris-HCl buffer, pH 8.0, containing 8 mol/L urea, 5 U/ml subtilisin and 0.05% TWEEN®-20 (polysorbate-20).

25 µl of calibrators or blood samples were mixed with 170 µl of extraction reagent in a tube and then incubated at 70° C. in water bath for 20 min. The tubes were removed from the water bath and recovered to room temperature.

25 µl processed blood sample/calibrator and 100 µl of TBST-BSA (50 mM Tris-HCl, pH 7.5, 0.9% NaCl, 0.05% TWEEN®-20 (polysorbate-20), 0.05% NaN3 and 0.5% BSA) containing 0.2 µg/ml of anti-FK506 monoclonal antibody (China Peptedes Co., Ltd, China) were added in microwells coated with a goat anti-mouse second antibody (Abcam). The mixture was incubated on a plate vibrator at room temperature (20° C.-25° C.) for 30 min.

50 µl of TBST-BSA containing 0.05 µg/ml of biotin labelled FK506 (Zhejiang HISUN pharmaceutical Co., Ltd, China) was added and incubated for another 30 min. The microwells were washed twice with TBST. 150 µl of TBST-BSA containing 2 µg/ml SA-Eu$^{3+}$ (SYM-BIO LifeScience Co., Ltd, Suzhou, China) was added and incubated on vibration for 20 min to bind the SA-Eu$^{3+}$ to the surface biotin.

The microwells were washed six times with TBST, enhancement solution (SYM-BIO Life-Science Co., Ltd, Suzhou, China) was added and incubated on vibration for 5 min. The fluorescence intensity was measured by a time-resolved fluorescence detector (Victor 1420, Perkin-Elmer). The FK506 concentration of the blood samples was determined according to the fluorescence intensity and calibration curve.

For data analysis, a fitted curve is obtained by plotting the FK506 calibrator concentration (X axis) versus the fluorescence intensity (Y axis) based on four parameters fitting. The drug concentration in samples can be determined by substituting the signal of the sample into the curve. The data analysis in the present disclosure can also use any specialized analysis software, such as ELISACalc, for rapid analysis of a number of samples.

Embodiment 2. The Effect of TWEEN®-20 (Polysorbate-20) at Different Concentrations in the Extraction Reagent on the FK506 Extraction In the embodiment, the extraction reagent is 50 mM Tris-HCl buffer (pH 8.0), containing 8 mol/L urea, 5 U/ml subtilisin and Tween 20 at different concentration. A set of calibrators with different concentrations of FK506 were prepared with human whole blood as matrix and detected according to the protocol of Embodiment 1. The result is shown in the FIG. 1.

As shown in FIG. 1, the fluorescence of FK506-TRFIA decreased with the increase of TWEEN®-20 (polysorbate-20) in the extraction reagent, and the fluorescence was decreased more obviously when the concentration of TWEEN®-20 (polysorbate-20) in the extraction reagent was more than 0.10%. Since 0.10%-0.20% of TWEEN®-20 (polysorbate-20) in the extraction reagent only brought an increase of 0.01%-0.02% of the total TWEEN®-20 (polysorbate-20) concentration in the reaction system. Such a low concentration of TWEEN®-20 (polysorbate-20) generally doesn't dissociate the surface second antibody or damage the antibody activity. So it is likely to be caused by the synergistic effect of urea and TWEEN®-20 (polysorbate-20), which dissociate the surface antibody of the microwells, leading to the decrease of the detection signal.

When the TWEEN®-20 (polysorbate-20) was removed from the extraction reagent of present disclosure, both of the inhibition and fluorescence intensity of the calibrators in the calibration curve were satisfactory, but about 20% of the blood samples clotted and adhered to the microwell surface during the detection process, this impaired the detection precision and caused deviation of the measured values. A low concentration of TWEEN®-20 (polysorbate-20) in the extraction reagent removed this problem. According to the embodiment, the concentration of TWEEN®-20 (polysorbate-20) in the extraction reagent of the present disclosure is preferably 0.02%-0.1% (v/v).

Embodiment 3. The Effect of the Protein Denaturant at Different Concentrations in the Extraction Reagent on the FK506 Extraction In the embodiment, the extraction reagent is 50 mM Tris-HCl buffer (pH 8.0), containing 0.05% (v/v) TWEEN®-20 (polysorbate-20), 5 U/ml subtilisin and urea or guanidine hydrochloride (protein denaturant) at different concentration. A set of calibrators with different concentrations of FK506 were prepared with human whole blood and detected according to the protocol as described in Embodiment 1. The result is shown in the FIG. 2.

Figure 2:
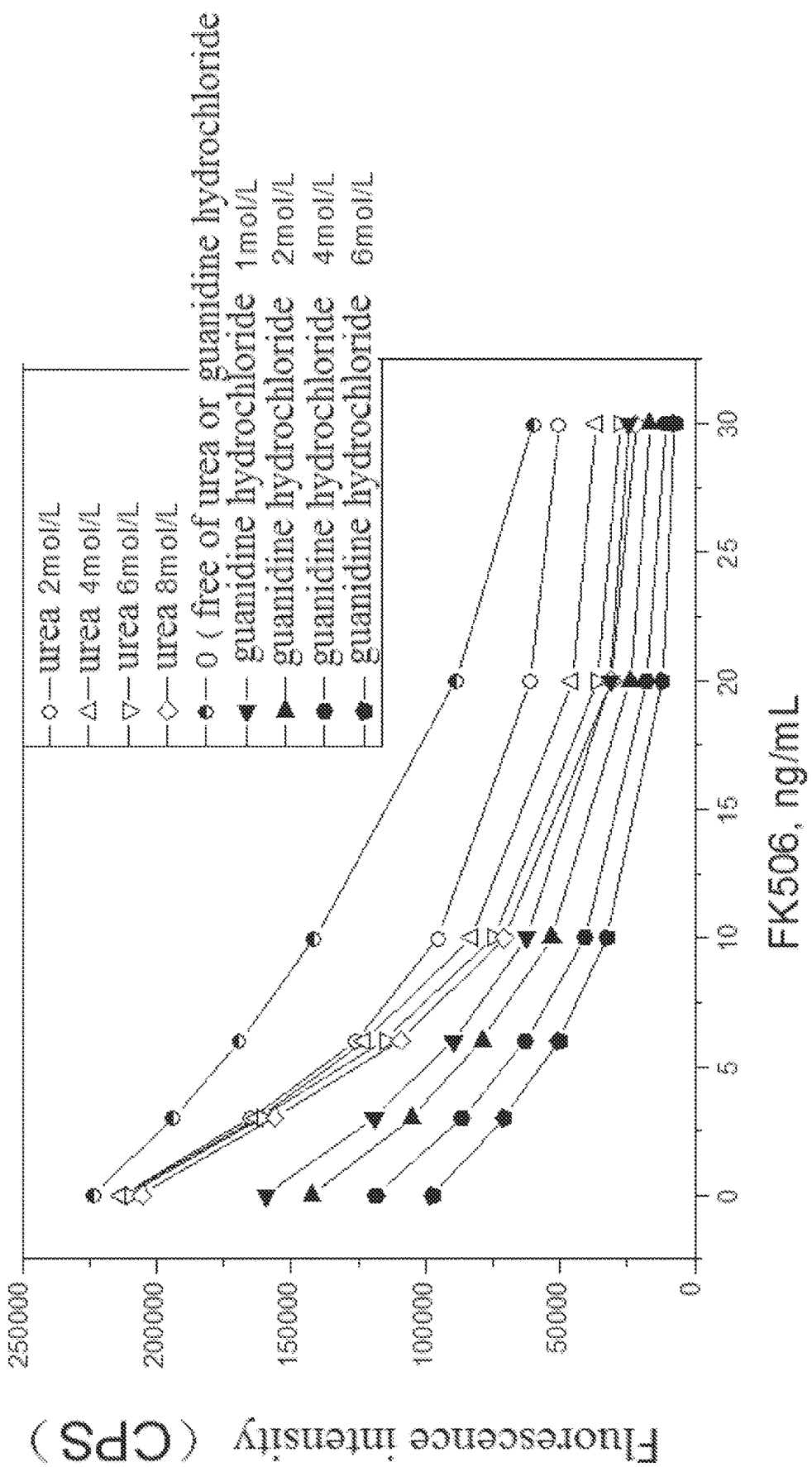
FIG. 2 shows the effect of protein denaturant at different concentrations in the extraction reagent on the FK506 extraction.

As shown in FIG. 2, the fluorescence of the calibrators decreased with the increase of the protein denaturant (urea or guanidine hydrochloride) in the extraction reagent, this was mainly due to the increased inhibition of the immunoreaction between the antibody and FK506 and the increased FK506 release at higher concentration of protein denaturants. When the protein denaturant was omitted from the extraction reagent (only contain the protease), the inhibition was relatively low while the fluorescence was high for the calibrators, indicating that the FK506 could not be fully released from its binding protein only with the action of the protease of the extraction reagent. In addition, when being treated by the extraction reagent without protein denaturant in it, the whole blood samples remained cloudy with bulky clots in it, this made it inconvenient for sampling and caused imprecision of the immunoassay.

As known from FIG. 2, when the urea in the extraction reagent was increased from 2 mol/L to 8 mol/L, the fluorescence of the calibrator-A with no FK506 in it and calibrator with low concentration of FK506 (such as 3 ng/mL) decreased only mildly, indicating the inhibition of the immunoreaction by urea was very weak; however, the fluorescence of the high concentration of FK506 calibrators (20 ng/mL-30 ng/mL) decreased sharply, indicating that only high concentration of urea can denature the protein and release FK506 effectively. When the concentration of urea in the extraction reagent was increased from 6 mol/L to 8 mol/L, the calibration curves of the FK506-TRFIA became consistent with similar fluorescence and inhibition ratios, indicating the function of urea at 6 mol/L-8 mol/L in the extraction reagent approached saturation. Compared with urea, guanidine hydrochloride show stronger denaturation for proteins. When the concentration of guanidine hydrochloride in the extraction reagent increased from 1 mol/L to 6 mol/L, the fluorescence of the calibrator-A with no FK506 drops obviously due to the strong inhibition of guanidine hydrochloride on the immunoreaction. At the same time, the fluorescence of the high concentration of FK506 calibrators dropped more rapidly than that of the low concentration of FK506 calibrators, this also indicated that the fully release of drug was partly dependent on the concentration of guanidine hydrochloride used.

Since the urea-based extraction reagent can release FK506 effectively and exerts only mild inhibition on the immunoreaction, and the sample treated by this extraction reagent can be converted to entirely transparent homogeneous solution, 6 mol/L-8 mol/L of urea is determined as the protein denaturant in the extraction reagent of the present disclosure.

Embodiment 4. The Effect of Protease at Different Concentrations in the Extraction Reagent on the FK506 Extraction With the presence of a urea or guanidine hydrochloride in the extraction reagent, the concentration of protease ought to be sufficient to promote cell lysis, protein denaturation and drug release in a short period of time. Concomitantly, the residual protease activity after sample extraction must be weak enough to avoid any adverse effect on the immunoreaction.

In the embodiment, the extraction reagent is 50 mM Tris-HCl buffer (pH 8.0), containing 0.05% (v/v) TWEEN®-20 (polysorbate-20), 8 mol/L urea and different concentration of subtilisin. A set of calibrators with different concentrations of FK506 were prepared with human whole blood as matrix and detected according to the protocol as described in Embodiment 1. The result is shown in the FIG. 3.

Figure 3:
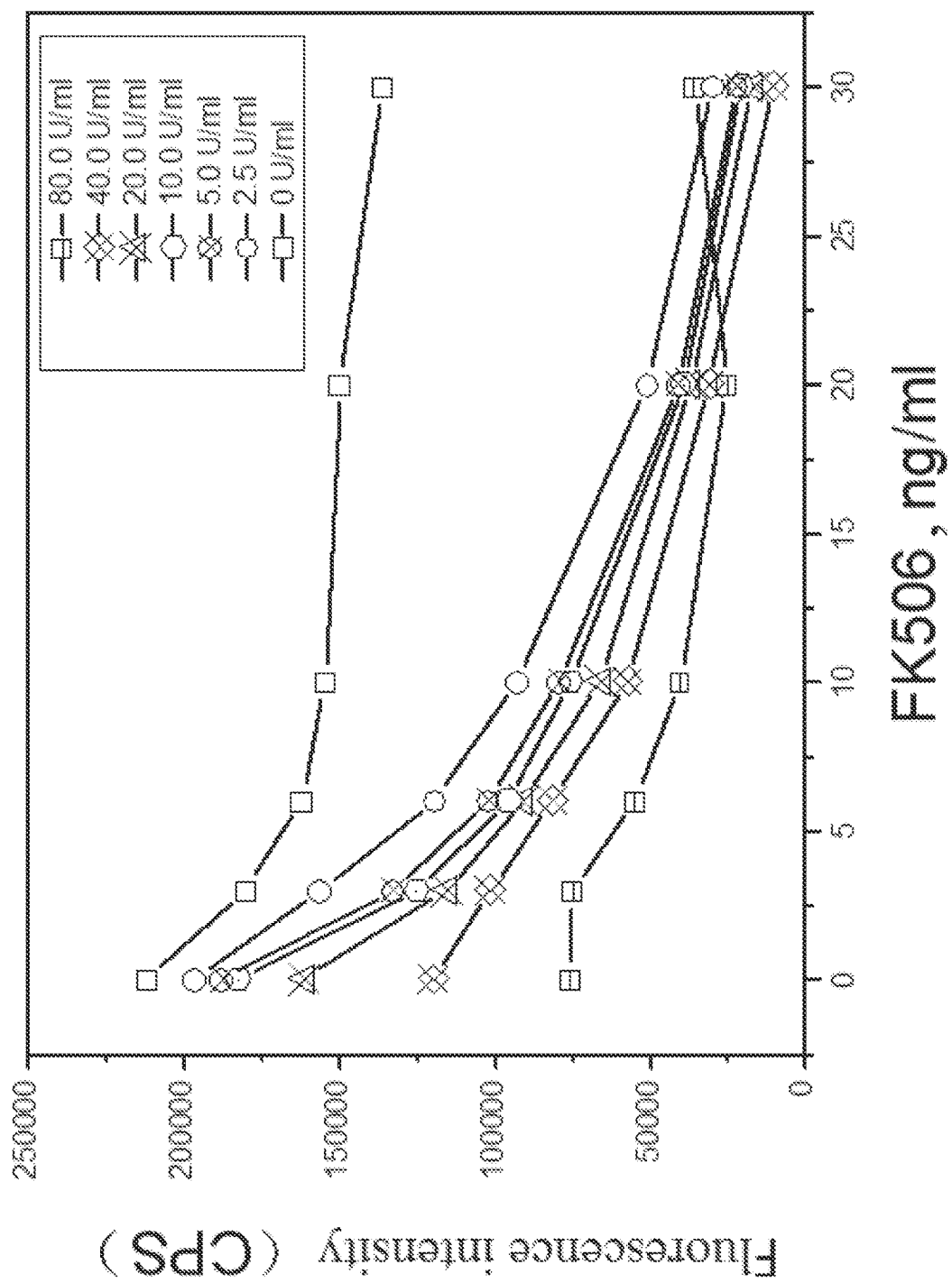
FIG. 3 shows the effect of protease at different concentrations in the extraction reagent on the FK506 extraction.

FIG. 3 shows that when the subtilisin was removed from the extraction reagent, the inhibition ratio of the calibrators with different concentration of FK506 was at a low level and show irregular change tendency, indicating most of the FK506 in the sample still remained to be bound by proteins. Also, the homogeneity of the samples processed by this extraction reagent was not ideal. When the concentration of subtilisin in the extraction reagent ranged from 2.5 U/ml to 10.0 U/ml, the inhibition ratio of the calibrators tend to be consistent and all the calibrators were turned to transparent amber-like solution after the treatment. Both the fluorescence intensity and inhibition ratio of the calibrators tend to be consistent when subtilisin was used in 5 U/ml to 10 U/ml. The fluorescence of the calibrators declined rapidly when subtilisin was more than 10 U/ml, this suggested that a high concentration of subtilisin could compromise the binding between the antibody and antigen. Based on above phenomena, the concentration of subtilisin used in the extraction reagent of the present disclosure was determined to be 2.5 U/ml to 10 U/ml.

Embodiment 5. The Effect of the Incubation Temperature in the Extraction Process on the Calibration Curve and Blood Sample Measurement In the embodiment, the extraction reagent is 50 mM Tris-HCl buffer (pH 8.0), containing 0.05% (v/v) TWEEN®-20 (polysorbate-20), 8 mol/L urea and 5 U/ml subtilisin. After mixing the sample with extraction reagent, the mixture was incubated for 20 min at different temperatures. The samples measured by FK506-TRFIA included a set of calibrators with different concentrations of FK506 and 12 EDTA anticoagulant whole blood samples with FK506 values determined by ABBOTT ARCHITECT 12000 CMIA system (The third affiliated hospital of the second military medical university of PLA). The FK506 values are listed in Table 1.

Above samples were also analysed by HPLC-MS/MS according to Li Pengfei et al. (Li Pengfei, Liu Lihong, Ma Ping et al.; LC-MS/MS method monitoring tacrolimus in human whole blood for therapeutic drug monitoring, Journal of Chinese mass spectrometry society, 2008, 29: 137-143). The FK506 values obtained were listed in Table 1.

TABLE 1

Impact of the incubation temperature in the extraction process on the measurement of FK506 in blood samples (ng/mL)

| | | HPLC-MS/MS (ng/mL) | | | | | | | | | | |
|---|---|---|---|---|---|---|---|---|---|---|---|---|
| | | 1.2 | 1.6 | 2.2 | 3.5 | 4.0 | 5.2 | 6.7 | 8.6 | 11.9 | 16.1 | 23 | 37 |
| | | CMIA (ng/mL) | | | | | | | | | | |
| | | 1.0 | 1.3 | 2.6 | 3.2 | 3.4 | 5.0 | 6.1 | 9.2 | 13.5 | 15.8 | 20.1 | >30 |
| FK506-TRFIA with temperature for drug extraction (ng/mL) | 90° C. | 1.0 | 1.1 | 1.3 | 2.6 | 3.1 | 3.1 | 4.1 | 5.5 | 5.8 | 8.5 | 12.1 | 15.6 |
| | 80° C. | 0.8 | 1.1 | 1.5 | 2.2 | 3.0 | 4.9 | 5.4 | 6.2 | 15.2 | 11.2 | 19.6 | 31.4 |
| | 70° C. | 1.1 | 1.4 | 2.5 | 3.3 | 3.7 | 5.0 | 5.8 | 9.5 | 12.7 | 14.9 | 21.5 | 35.9 |
| | 60° C. | 0.4 | 1.3 | 1.6 | 2.6 | 2.9 | 4.0 | 5.3 | 8.8 | 10.0 | 9.9 | 15.5 | 29.4 |
| | 50° C. | 0.1 | 0.5 | 0.8 | 1.2 | 1.1 | 1.5 | 1.9 | 2.3 | 3.8 | 6.1 | 9.9 | 21.6 |
| | 40° C. | 0.5 | 1.2 | 1.8 | 2.2 | 3.4 | 4.5 | 4.6 | 3.7 | 9.4 | 11.2 | 15.9 | 29.9 |
| | 30° C. | 0.3 | 1.7 | 1.9 | 3.0 | 2.9 | 4.7 | 5.1 | 4.6 | 9.9 | 15.0 | 18.9 | 22.7 |

Figure 4:
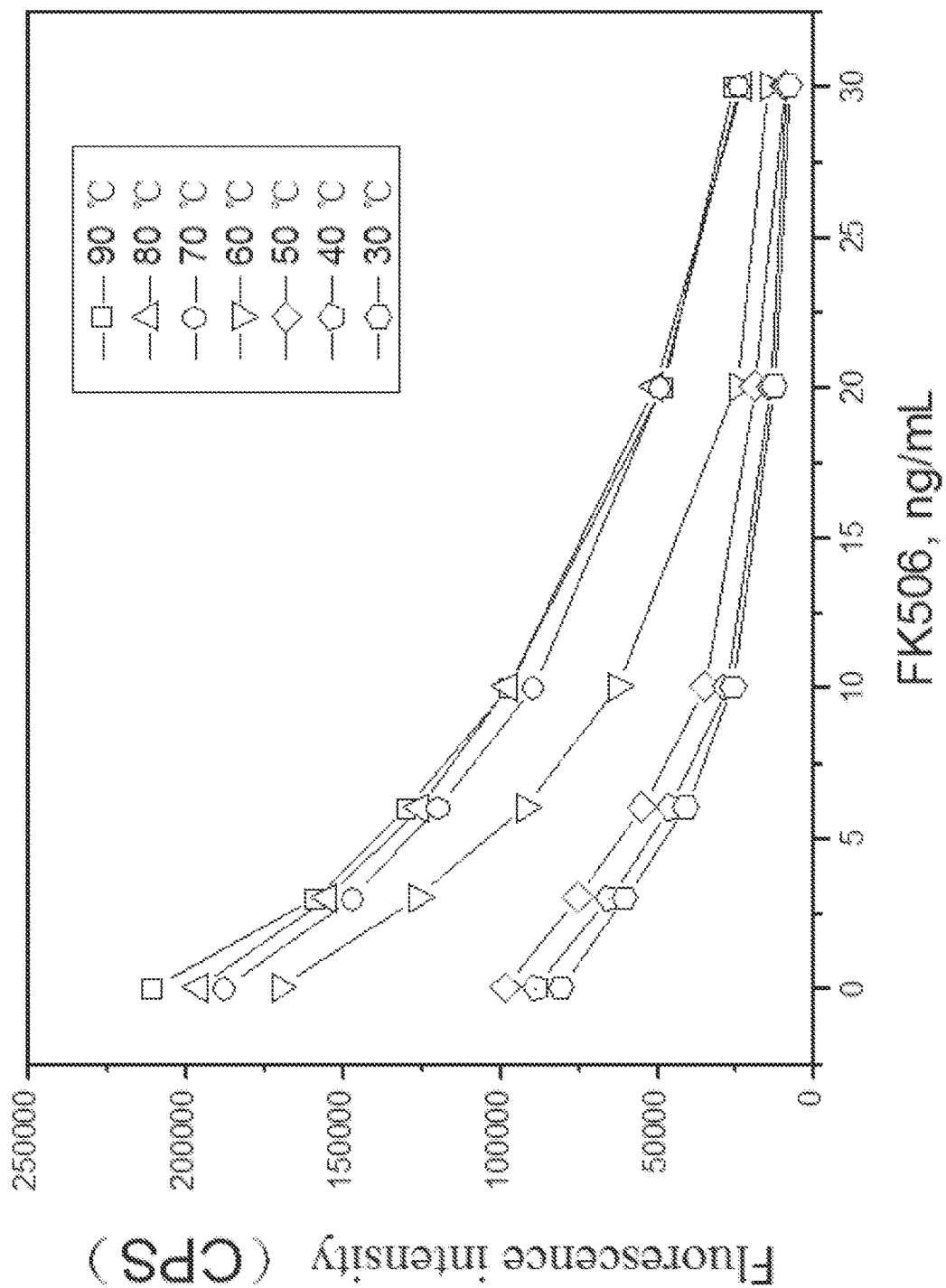
FIG. 4 shows the effect of temperature in the sample extraction incubation on the calibration curve.

In the present disclose, the blood sample and extraction reagent need to be heated and incubated to make the protease action fully for enzymolysis, and in the meanwhile, most of the protease activity need to be inactivated to alleviate its adverse effect on the activity of antibody in the subsequent immunoreaction. As shown in Table 1 and FIG. 4, when the samples were extracted at temperature below 60° C., the fluorescence intensity decreased obviously as the decrease of the temperature for sample extraction, the FK506 concentrations obtained were fluctuated irregularly and lower than that of the reference method HPLC-MS, suggesting that low incubation temperature for the sample extraction was not effective enough to dissolve cells, denature proteins and release the drugs. In the meantime, when the extraction incubation was performed at low temperature, the protease activity survived from the extraction process exerted an adverse effect on the activity of both of the solid phase second antibody and anti-FK506 antibody, leading to a fluorescence decrease. When the extraction incubation was performed at 70° C.-80° C., the calibration curves had relatively strong fluorescence and stable inhibition ratios. With the extraction incubation at 70° C., the FK506 values of the samples by FK506-TRFIA show good consistence with both HPLC-MS/MS and FK506 CMIA. The FK506 values tend to decrease when the incubation temperature for sample extraction was increased to 90° C. Based on above data, the incubation temperature for the sample treatment by present extraction reagent was chosen to be 60° C.-80° C.

Embodiment 6. The Impact of Incubation Time in the Sample Extraction Process on the Calibration Curve and Measurement of Blood Samples In the embodiment, the extraction reagent is 50 mM Tris-HCl buffer, pH 8.0, it contains 0.05% (v/v) TWEEN®-20 (polysorbate-20), 8 mol/L urea and 5 U/ml subtilisin. A set of calibrators with different concentrations of FK506 prepared with human whole blood as metrix and twelve EDTA anticoagulated blood samples with FK506 values determined by ABBOTT FK506 CMIA (the Third affiliated hospital of the Second military medical university of PLA (Shanghai, China) were analyzed. After the samples were mixed with the extraction reagent, the incubation time for extraction was evaluated by changing the time at 70° C.

Figure 5:
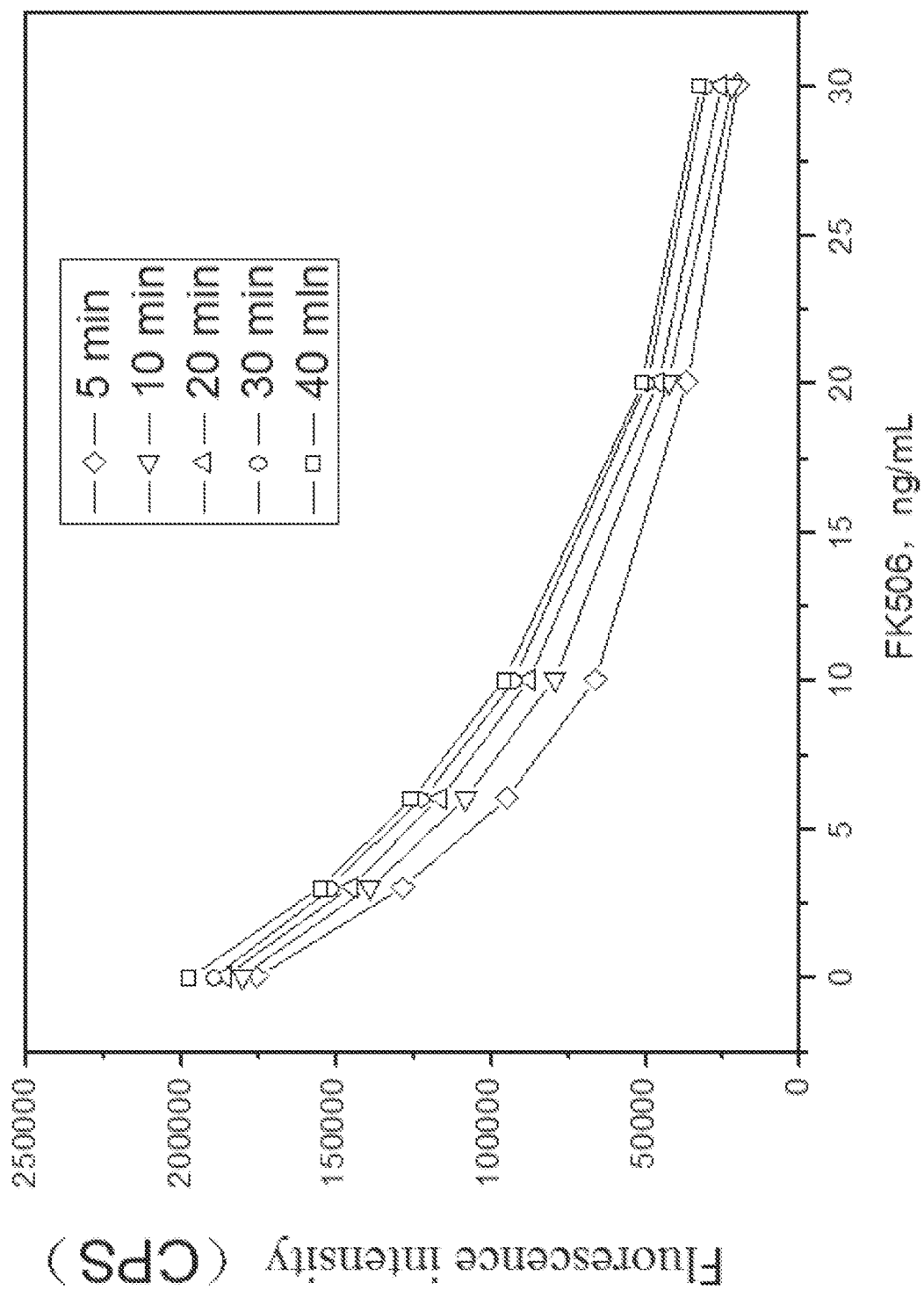
FIG. 5 shows the impact of incubation time in the sample extraction process on the calibration curve.

FIG. 5 show the fluorescence of the calibrators of FK506-TRFIA increased as the increase of incubation time from 5 min to 40 min in the sample extraction process, the fluorescence increased more significantly when the incubation prolong form 5 min to 10 min. It suggested that when the incubation time was less than 10 min, the residue protease in the system was likely to hydrolyse the antibodies, leading to a decreased signal. Within the incubation time from 5 min to 40 min, the FK506 values of the samples show good consistency with HPLC-MS and FK506 CMIA (Table 2). Since relatively longer incubation time gave rise to smaller residual protease activity, the incubation time for sample treatment in present disclosure was selected to be 10 min-30 min.

The samples were processed by DiaSorin extraction reagent: 50 μL of the whole blood sample and 300 μL of enzymolysis solution (Sorin medical co., LTD, Shanghai, China; Lot #305102) were pipetted into centrifuge tubes. After being vortexed for 20 seconds, the mixture was incubated at room temperature for 15 minutes, and then incubated in 75° C. water bath for another 15 minutes. The tubes were removed from the bath, vortexed for 20 seconds and centrifuged at 1800×g for 10 minutes. The supernatant was used as sample.

The samples were processed by ABBOTT extraction reagent: 200 μL of the whole blood sample and 200 μL Whole Blood Precipitation Reagent (Abbott Laboratories Trading Co. Ltd., Shanghai, China; 309221) were pipetted into centrifuge tubes. After 10 seconds of vortex the mixture was centrifuged at 10000×g for 5-6 minutes. The supernatant was used as sample.

The sample treatment by the extraction reagent of the present disclosure was performed as described in embodiment 1.

Figure 6:
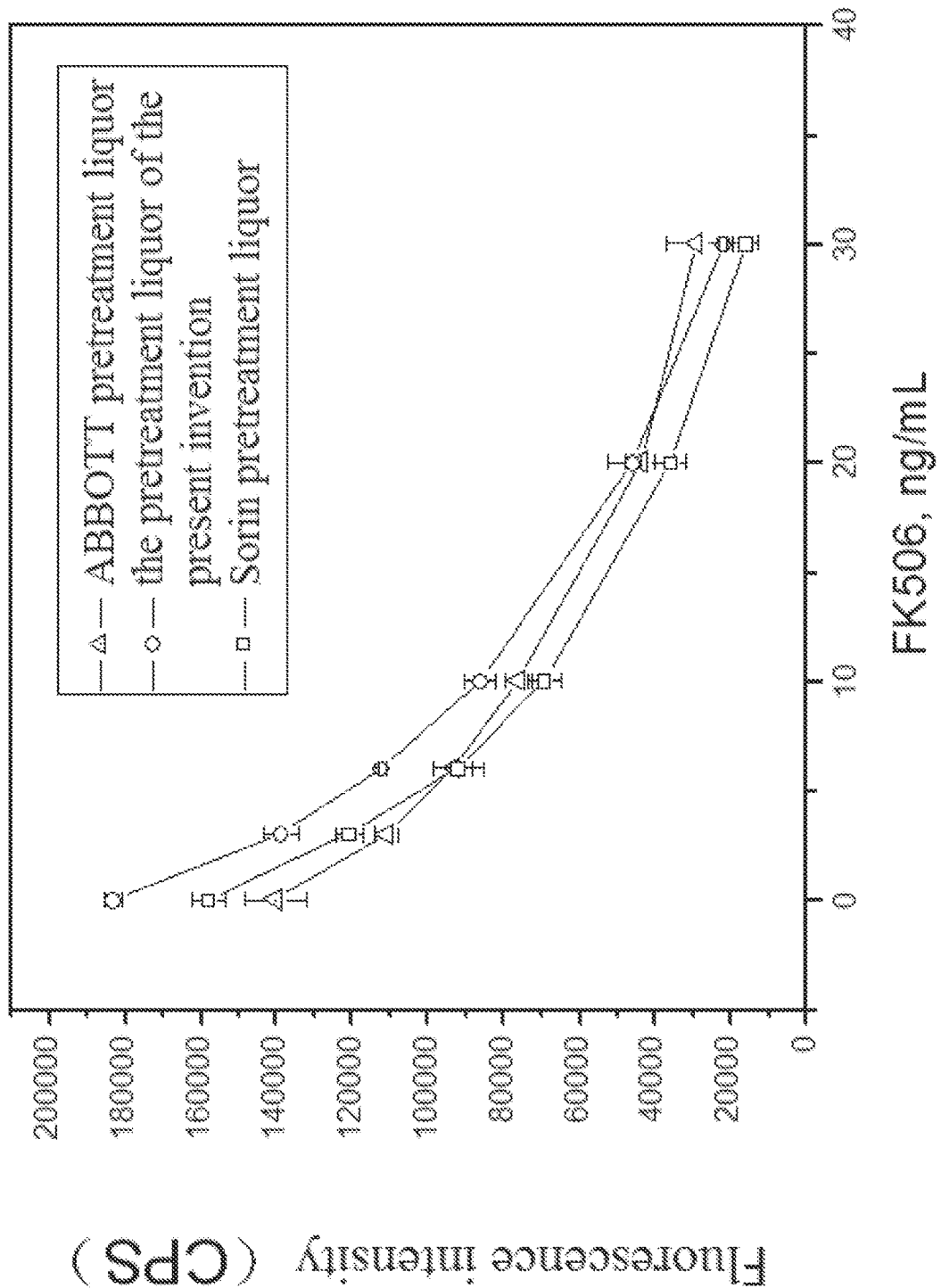
FIG. 6 shows the impact of three extraction reagents on the calibration curves.
Figure 7A:
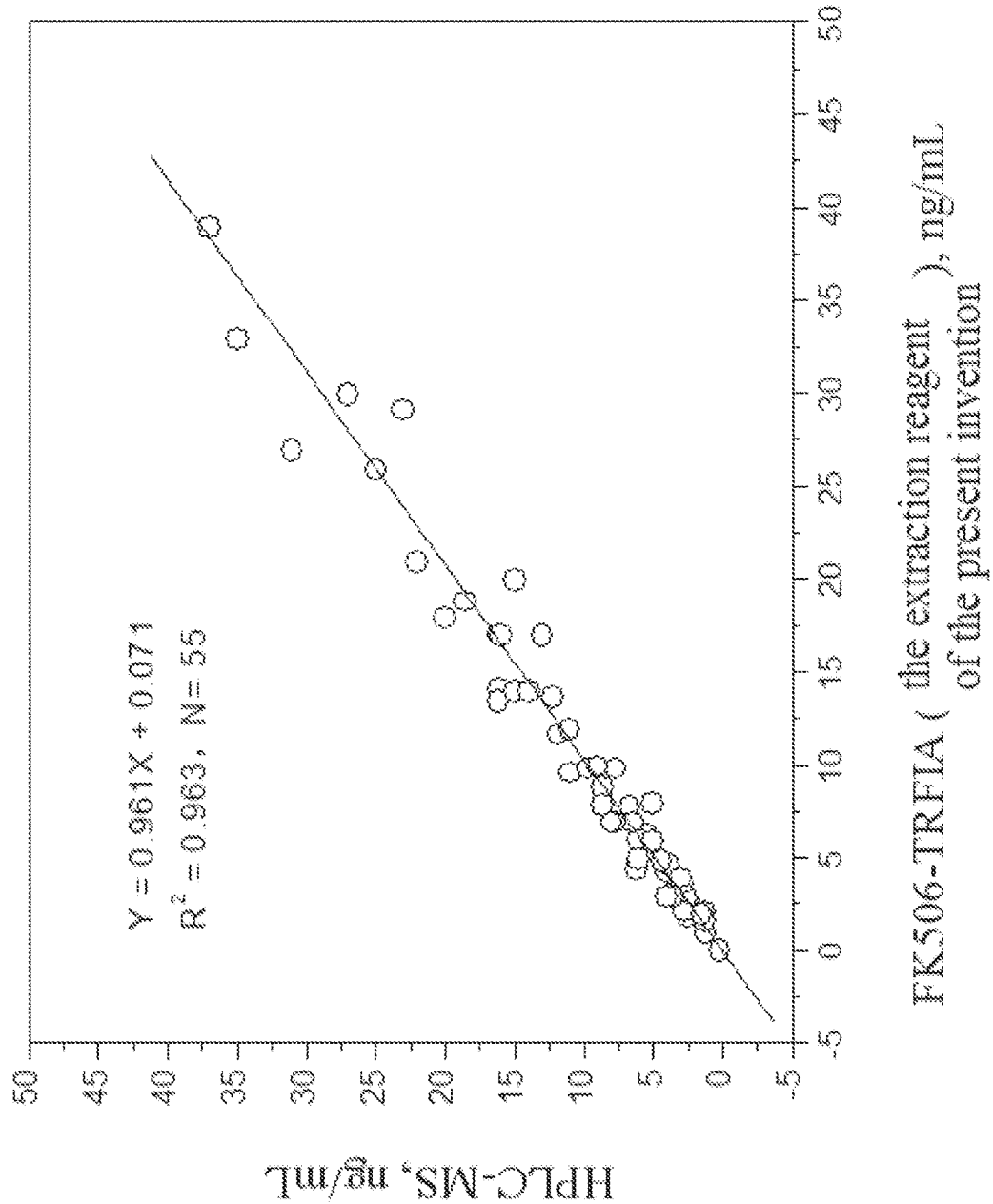
FIG. 7A shows the correlation of the measurements by HPLC-MS/MS and the FK506-TRFIA using the extraction reagent of present disclosure.
Figure 7B:
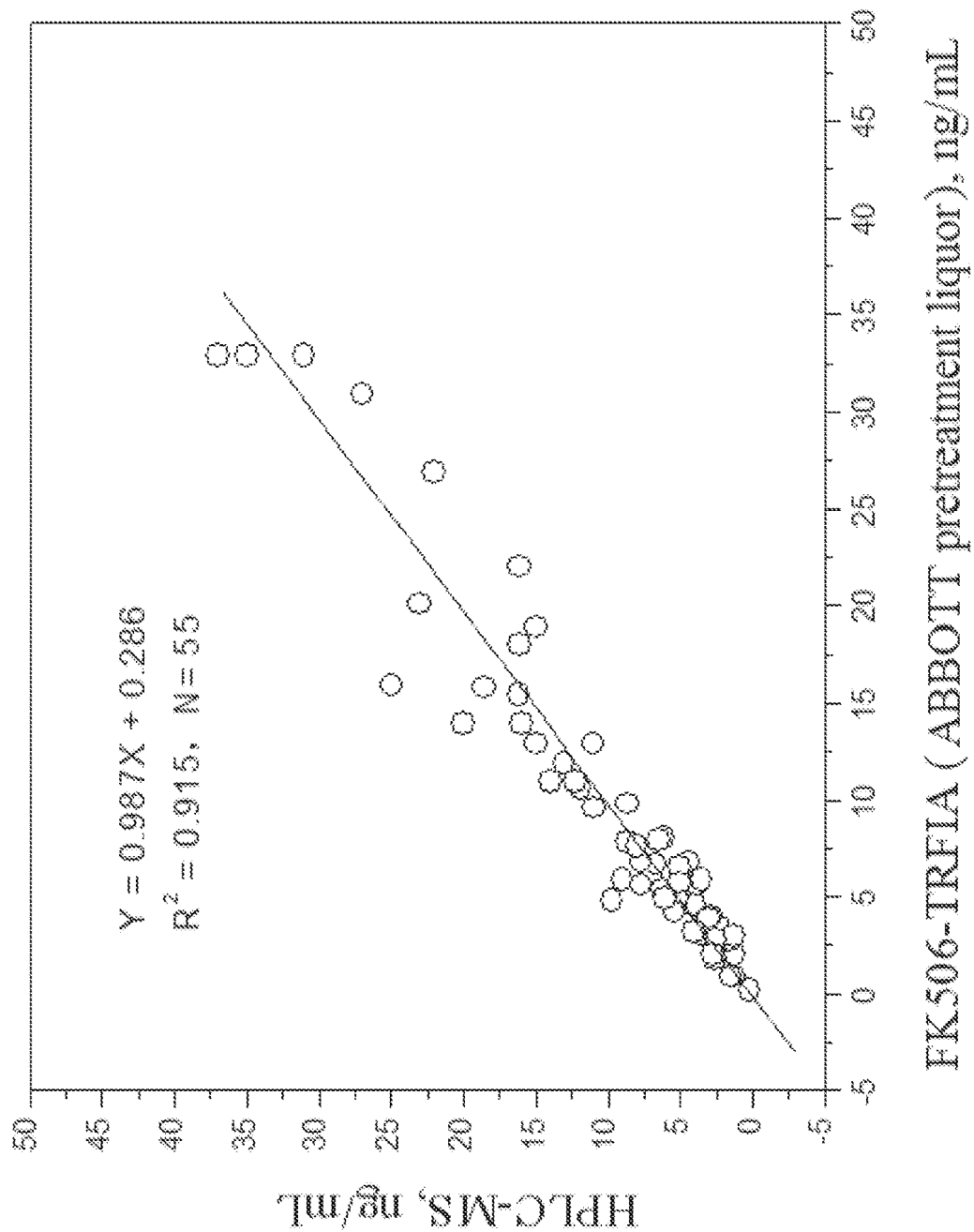
FIG. 7B shows the correlation of the measurements by HPLC-MS/MS and the FK506-TRFIA using the extraction reagent from CMIA kit (ABBOTT-12000).
Figure 7C:
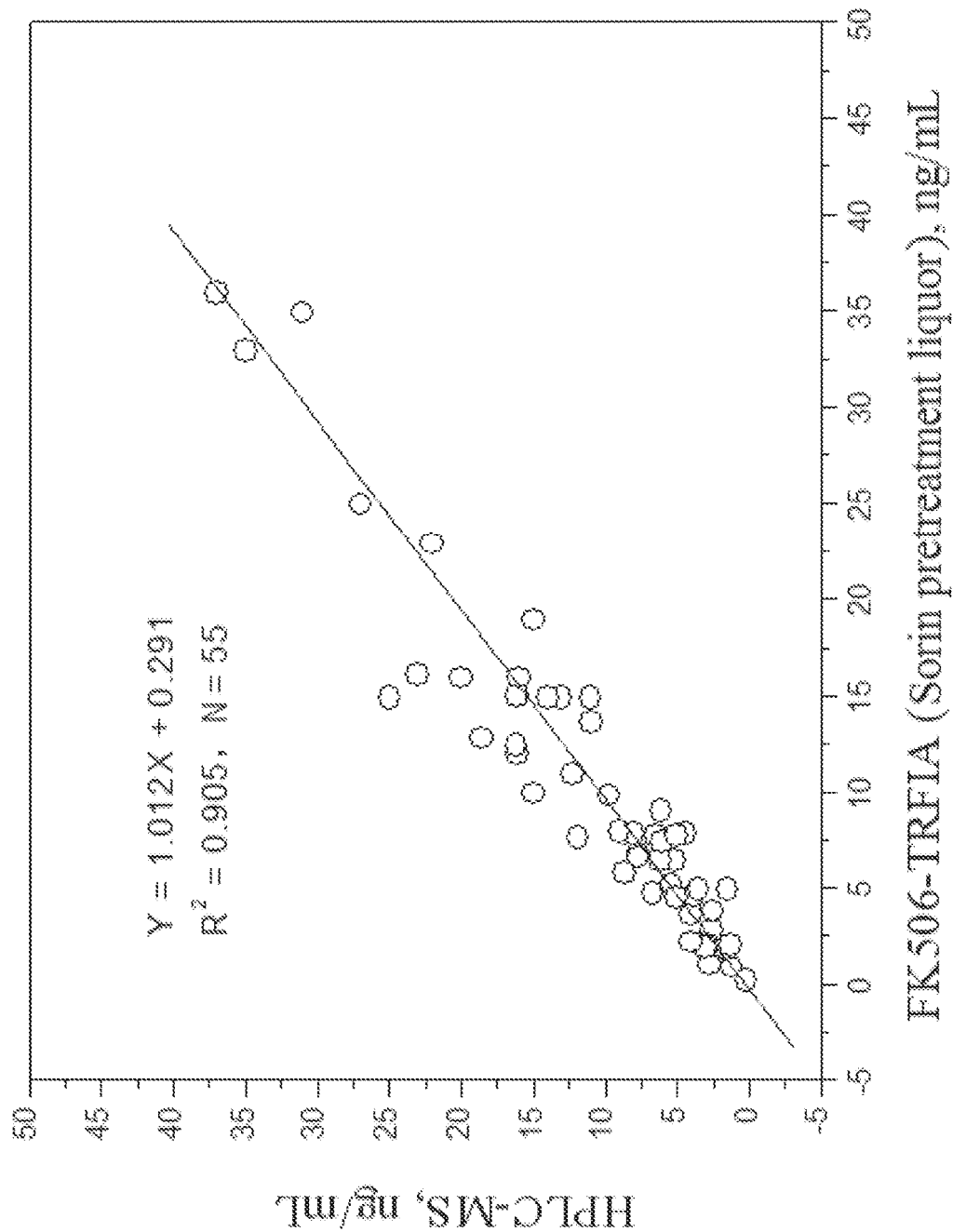
FIG. 7C shows the correlation of the measurements by HPLC-MS/MS and FK506-TRFIA using the extraction reagent from PRO-Trac™ II Tacrolimus ELISA Kit (DiaSorin).

55 EDTA anticoagulant whole blood samples (The third affiliated hospital of the second military medical university of PLA) with FK506 values determined by HPLC-MS were processed by the three extraction reagents as described above. The processed samples were measured by FK506-TRFIA according to the protocol of embodiment 1. With HPLC-MS as the reference method, the effect of the three extraction reagents on FK506-TRFIA was evaluated by comparison of the calibration curves (each calibrator was determined in quadruplicate; FIG. 6) and the FK506 values (FIGS. 7A, 7B and 7C).

As given in FIG. 6, the calibration curve of FK506-TRFIA based on ABBOTT 12000 extraction reagent had relatively low fluorescence and less precision in the quadruplicate measurement for the calibration curve, indicating an adverse effect of the organic solvent of the extraction reagent on the immunoreaction system. The calibration

TABLE 2

The impact of incubation time in the extraction process on the measurement of blood samples (ng/mL)

| | | HPLC-MS/MS (ng/mL) | | | | | | | | | | |
|---|---|---|---|---|---|---|---|---|---|---|---|---|
| | | 1.2 | 1.6 | 2.2 | 3.5 | 4 | 5.2 | 6.7 | 8.6 | 11.9 | 16.1 | 23 | 37 |
| | | CMIA (ng/mL) | | | | | | | | | | |
| | | 1 | 1.3 | 2.6 | 3.2 | 3.4 | 5 | 6.1 | 9.2 | 13.5 | 15.8 | 20.1 | >30 |
| FK506 TRFIA with different incubation time for extraction (ng/mL) | 5 min | 1.3 | 1.5 | 1.9 | 3.0 | 4.9 | 5.8 | 6.1 | 7.5 | 10.8 | 18.2 | 25.3 | 33.5 |
| | 10 min | 0.9 | 1.6 | 2.8 | 3.8 | 4.1 | 5.9 | 6.8 | 11.2 | 12.8 | 16.8 | 26.9 | 35.1 |
| | 20 min | 1 | 1.9 | 2.5 | 3.2 | 4.3 | 5.5 | 7.8 | 8.9 | 11.7 | 17.1 | 22.2 | 35 |
| | 30 min | 1.2 | 1.6 | 2 | 3.1 | 3.9 | 4.3 | 6.3 | 8 | 9.4 | 15.2 | 22.9 | 32.1 |
| | 40 min | 1.4 | 1.5 | 1.8 | 3.2 | 4.3 | 6 | 7.2 | 10.2 | 13.2 | 15.8 | 20.4 | 35.8 |

Embodiment 7. Experimental Comparison of Different Extraction Reagents

In the embodiment, the effect of three extraction reagents, including that from the DiaSorin PRO-Trac™ II Tacrolimus ELISA Kit, that from the ABBOTT FK506 CMIA Kit (ARCHITECT 12000 System) and that from the present disclosure, were compared with regard to the calibration curve and sample measurement values in the FK506-TRFIA of the present disclosure.

curves based on the extraction reagents from both of the DiaSorin and the present disclosure were nearly paralleled with good precision, but the fluorescence obtained using the extraction reagent of the present disclosure is higher, demonstrating a milder influence of the extraction reagent of present disclosure on the reaction system besides its effectiveness on releasing drug.

As shown in FIGS. 7A, 7B and 7C, for the 55 blood samples treated by the above three extraction reagents, the correlation coefficients of HPLC-MS/MS with FK506-TRFIA using above three extraction reagents, namely that of the present disclosure, that from ABBOTT ARCHITECT Tacrolimus CMIA KIT and PRO-Trac™ 11 Tacrolimus ELISA KIT, were 0.981, 0.957 and 0.951, respectively, it demonstrated the FK506-TRFIA based on the extraction reagent of the present disclosure had the best consistency with the reference method.

What is claimed is:

1. A method for detecting immunosuppressant drug in a whole blood sample, comprising:
    processing the whole blood sample by mixing with an extraction reagent of the immunosuppressant drug while heating the mixture to obtain a homogeneous solution, wherein processing the whole blood sample by mixing with the extraction reagent extracts the immunosuppressant drug from the whole blood sample without using organic solvent; and then
    determining a concentration of the immunosuppressant drug contained in the mixture directly without centrifugation using an immunoassay,
    wherein the extraction reagent comprises a protein denaturant, a proteolytic enzyme, a surfactant and a pH buffer,
    wherein the protein denaturant is selected from urea or guanidine hydrochloride, wherein a molar concentration of the urea in the extraction reagent is 4 mol/L to 12 mol/L, and alternatively wherein a molar concentration of the guanidine hydrochloride in the extraction reagent is about 1 mol/L to 8 mol/L, wherein the surfactant is selected from one or more of polysorbate-20, saponin and polyethylene glycol octyl phenyl ether.

2. The method according to claim 1, wherein a molar concentration of the urea in the extraction reagent is 6 mol/L to 8 mol/L; and alternatively a molar concentration of the guanidine hydrochloride in the extraction reagent is 2 mol/L to 6 mol/L.

3. The method according to claim 1, wherein the proteolytic enzyme is selected from one or more of subtilisin, protease K and dispase.

4. The method according to claim 3, wherein the proteolytic enzyme is subtilisin.

5. The method according to claim 4, wherein an amount of the subtilisin used in the extraction reagent is 2.5 U/ml to 10 U/ml.

6. The method according to claim 1, wherein the surfactant is polysorbate-20.

7. The method according to claim 6, wherein a volume ratio of the polysorbate-20 in the extraction reagent is 0.005% to 1% (v/v).

8. The method according to claim 7, wherein the volume ratio of the polysorbate-20 in the extraction reagent is 0.02% to 0.1% (v/v).

9. The method according to claim 1, wherein a pH value of the buffer is between 6.5 and 8.5.

10. The method according to claim 9, wherein a heating temperature is 50° C.-90° C., and a heating time is 5 min-50 min.

11. The method according to claim 10, wherein the heating temperature is 60° C.-80° C., and the heating time is 10 min-30 min.

12. The method according to claim 1, wherein the immunosuppressant drug comprises tacrolimus, sirolimus, everolimus, zotarolimus or cyclosporin A.

13. The method according to claim 1, wherein when processing the whole blood sample, a volume ratio of the whole blood sample to the extraction reagent is 1/1 to 1/10.

14. The method according to claim 13, wherein when processing the whole blood sample, the volume ratio of the blood sample to the extraction reagent is 1/2 to 1/5.

* * * * *